Figure 1:
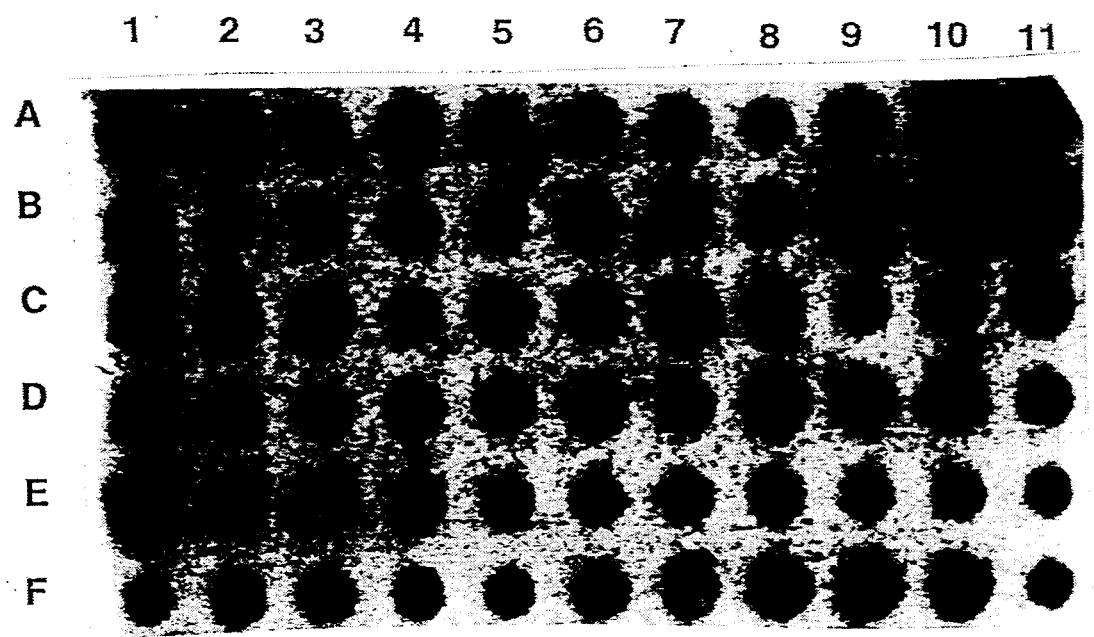
Figure 2:
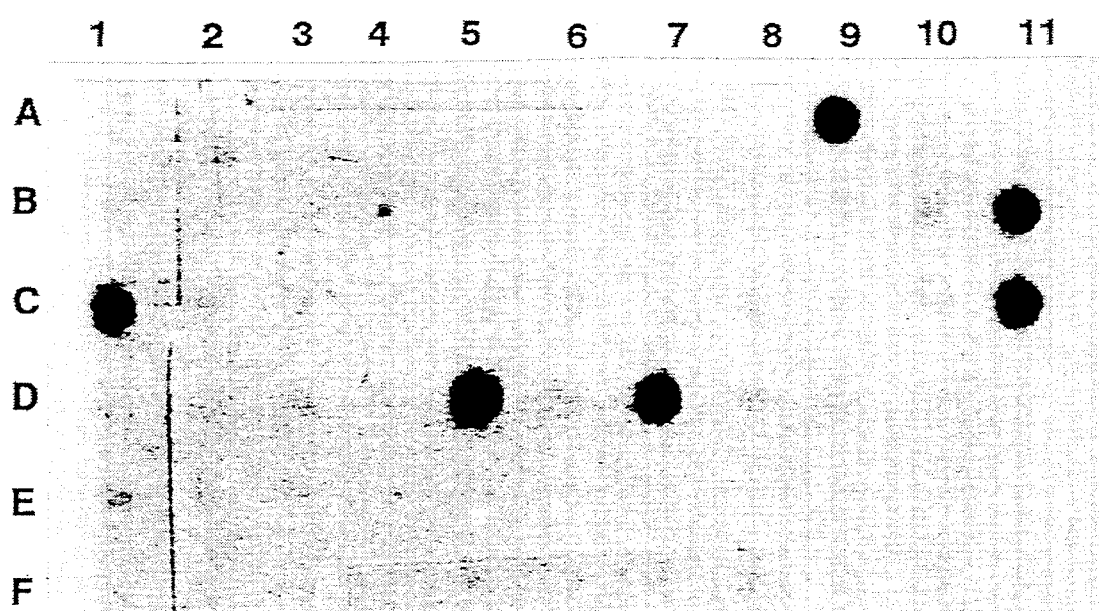

United States Patent [19]

Gaertner et al.

[11] Patent Number: 5,430,137
[45] Date of Patent: Jul. 4, 1995

[54] **PROBES FOR THE IDENTIFICATION OF *BACILLUS THURINGIENSIS* ENDOTOXIN GENES**

[75] Inventors: Frank H. Gaertner, San Diego; August J. Sick, Oceanside; Mark Thompson, Del Mar; H. Ernest Schnepf, San Diego; George E. Schwab, La Jolla; Kenneth E. Narva, San Diego, all of Calif.

[73] Assignee: Mycogen Corporation, San Diego, Calif.

[21] Appl. No.: 968,781

[22] Filed: Oct. 30, 1992

Related U.S. Application Data

[63] Continuation-in-part of Ser. No. 737,569, Jul. 26, 1991, Pat. No. 5,204,237, which is a continuation of Ser. No. 427,068, Oct. 25, 1989, abandoned.

[51] Int. Cl.$^6$ .................. C07H 21/04; C12Q 1/68
[52] U.S. Cl. .................... 536/24.32; 435/6; 935/77; 935/78
[58] Field of Search ............. 435/6; 536/23.1, 23.7, 536/23.71, 24.32

[56] References Cited

U.S. PATENT DOCUMENTS 5,126,133  6/1992  Payne et al. .................. 424/93

FOREIGN PATENT DOCUMENTS 0358557  9/1989  European Pat. Off. ............. 435/6

OTHER PUBLICATIONS

Gaertner, Frank, and Leo Kim (1988) "Current Applied Recombinant DNA Projects" TIBTECH 6:S4–S7.

Gaertner, Frank (1990) "Cellular delivery systems for insecticidal proteins: living and non-living microorganisms" Controlled Delivery of Crop-Protection Agents pp. 245–257.

Hofte, Herman, and H. R. Whiteley (1989) "Insecticidal Crystal Proteins of *Bacillus thuringiensis*" Microbiological Reviews 53(2):242–255.

Carozzi, Nadine B., Vance C. Kramer, Gregory W. Warren, Stephen Evola, and Michael G. Koziel (1991) "Prediction of Insecticidal Activity of *Bacillus thuringiensis* Strains by Plymerase Chain Reaction Product Profiles" Applied and Environmental Microbiology 57(11):3057–3061.

Feitelson, Jerald S., Jewel Payne, and Leo Kim (1992) "*Bacillus thuringiensis:* Insects and Beyond" Bio/Technology 10:271–275.

*Primary Examiner*—Stephanie W. Zitomer
*Attorney, Agent, or Firm*—Saliwanchik & Saliwanchik

[57] ABSTRACT

This invention concerns novel gene probes which can be used to identify DNA from *Bacillus thuringiensis* microbes which encode protein endotoxins. The invention probes greatly facilitate the search for useful microbes hosting genes which encode toxins.

4 Claims, 2 Drawing Sheets

PROBES FOR THE IDENTIFICATION OF *BACILLUS THURINGIENSIS* ENDOTOXIN GENES

CROSS-REFERENCE TO A RELATED APPLICATION

This is a continuation-in-part of application Ser. No. 07/737,569, filed Jul. 26, 1991, now U.S. Pat. No. 5,204,237; which is a continuation of application Ser. No. 07/427,068, filed Oct. 25, 1989, now abandoned.

BACKGROUND OF THE INVENTION

The soil microbe *Bacillus thuringiensis* (B.t.) is a Gram-positive, spore-forming bacterium characterized by parasporal crystalline protein inclusions. These often appear microscopically as distinctively shaped crystals. The proteins are highly toxic to pests and specific in their activity. The toxin genes have been isolated and sequenced, and recombinant DNA-based B.t. products produced and approved. In addition, with the use of genetic engineering techniques, new approaches for delivering B.t. endotoxins to agricultural environments are under development, including the use of plants genetically engineered with endotoxin genes for insect resistance and the use of stabilized intact microbial cells as B.t. endotoxin delivery vehicles (Gaertner, F. H., L. Kim [1988] TIBTECH 6:S4–S7). Thus, isolated B.t. endotoxin genes are becoming commercially valuable.

Over the past 30 years, commercial use of B.t. pesticides has been largely restricted to a narrow range of Lepidopteran (caterpillar) pests. Preparations of the spores and crystals of *B. thuringiensis* subsp. *kurstaki* have been used for many years as commercial insecticides for lepidopteran pests. In recent years, however, investigators have discovered B.t. pesticides with specificities for a much broader range of pests.

Other varieties of B.t., namely *israelensis* and *san diego*, have been used commercially to control insects of the orders Diptera and Coleoptera, respectively (Gaertner, F. H. [1989] "Cellular Delivery Systems for Insecticidal Proteins: Living and Non-Living Microorganisms," in *Controlled Delivery of Crop Protection Agents*, R. M. Wilkins, ed., Taylor and Francis, New York and London, 1990, pp. 245–255).

Recently, many new subspecies of B.t. have been identified, and many genes responsible for active δ-endotoxin proteins have been isolated (Höfte, H., H. R. Whiteley [1989] *Microbiological Reviews* 52(2):242–255). Höfte and Whiteley classified 42 B.t. crystal protein genes into 14 distinct genes, grouped into 4 major classes based on amino-acid sequence and host range. The classes were CryI (Lepidoptera-specific), CryII (Lepidoptera- and Diptera-specific), CryIII (Coleoptera-specific), and CryIV (Diptera-specific). The discovery of strains specifically toxic to protozoan pathogens, animal-parasitic liver flukes (Trematoda), ants, or mites (Acari) has broadened the potential B.t. product spectrum even further. With activities against unique targets, these novel strains retain their very high biological specificity, and nontarget organisms remain unaffected. The availability of a large number of diverse B.t. toxins may also enable farmers to adopt product-use strategies that minimize the risk that B.t.-resistant pests will arise.

Thus, many different B.t. toxins are now known. However, to date, the method for isolating the responsible toxin genes has been a slow empirical process. That is, for a given B.t. isolate, there is currently no rapid systematic method for identifying the responsible toxin genes or for predicting the activity of a given B.t. isolate. Currently, a given B.t. isolate must first be placed through a tedious series of bioassays to determine its spectrum of insecticidal activity, and subsequently an attempt is made to isolate the genes responsible for the observed insecticidal activity, generally through the nonsystematic use of mixed or randomly selected oligomeric probes.

The subject invention eliminates some of the empirical nature of finding certain B.t. insecticidal protein toxin genes. Although the process is still highly unpredictable, this invention facilitates expedient identification of potentially new commercially valuable insecticidal endotoxin genes.

Although a recent report of such methods has appeared (see Carozzi, N. B., V. C. Kramer, G. W. Warren, S. Evola, G. Koziel [1991] *Appl. Env. Microbiol.* 57(11):3057–3061), this report postdates our original filing date and does not disclose or suggest the specific probes of the subject invention. Also, EP 0 358 557 AZ discloses an amino acid sequence which has sequence similarity to SEQ ID NO. 1, below, but it is 30% longer.

BRIEF SUMMARY OF THE INVENTION

The subject invention concerns unique nucleotide sequences which are highly useful as probes to detect genes coding for *Bacillus thuringiensis* toxins. We provide herein many such nucleotide sequences. Also described are peptides wherein the nucleotide sequences which code for the peptides can be used as probes.

A unique and advantageous feature of the invention is the provision of a probe library comprising probes of varying specificity. There are probes which identify a broad range of B.t. toxin genes (universal probes) and other probes which identify only specific genes or sets of genes (sub-universal, group-specific, or gene-specific probes).

Thus, the subject invention concerns (1) peptide and corresponding nucleotide sequences which identify proteins and responsible genes broadly (universally) as B.t. endotoxins, and specifically as nematode-, lepidopteran-, dipteran-, coleopteran-, ant-, or mite-active endotoxins, and (2) the use of such nucleotide segments as either universal, group, or gene-specific probes for the systematic identification and isolation of endotoxin genes.

Specifically, the invention concerns the following sequences:

(i) a peptide sequence whose single letter amino acid designation is "YIDKIEFIP" (SEQ ID NO. 1) or variations thereof which embody point mutations according to the following: position 1, Y or I, L, V, F, or H; position 2, I or L; position 3, D or E; position 4, K or R; position 5, F or L; position 7, F or I or L; position 8, I or V or L; position 9, P or L; and whose corresponding nucleotide sequence specifies the following universal nucleotide probes: 5'-"TGGAATAAATTCAATT(C or T)(T or G)(A or G)TC(T or A)A"3' (SEQ ID NO. 2); "5'-TAGA(T or C)A(A or G)AATTGAATTTAT(A or T)C"-3' (SEQ ID NO. 3); "5'-TTTAGATCGT(A or C)TTGA(G or A)TTT(A or G)T(A or T)CC-3'" (SEQ ID NO. 4); "5'-AGGAACAAA(T or C) TCAA(T or G)(T or A)CG(A or G)TCTA-3'" (SEQ ID NO. 5); "5'-TATAGATAGAATCGAATT(C or T)(A or G or C)T(G or C or T)CC-3'" (SEQ ID NO. 6); "5'-TATAGATAAAATAGAATT(G or T) (A or G)T(A or C or T)C-3'" (SEQ ID NO. 7); "5'-TATAGATAGAAT(A or T)GAATT(C or T)(A or G)T(A or G or C or T)C-3'" (SEQ ID NO. 8); "5'-GAATAAATTCTATT(C or C) (T or G or C)(G or C or A)TCTA-3'" (SEQ ID NO. 9); "5'-GGAACAAA(T or C)TCAA(T or G)(T or C)CG(G or A)TCTA-3'" (SEQ ID NO. 10); or "5'-GGAATAAATFCAATT(T or G) (T or A)(G or A)TC(T or A)A-3'" (SEQ ID NO. 11). These probes detect nematode, coleopteran, lepidopteran, mite, ant, or dipteran-active endotoxin genes;

(ii) a peptide sequence whose single letter amino acid designation is "GPGFFGGD" (SEQ ID NO. 12) and whose nucleotide sequence specifies the universal nucleotide probe "5'-GGACCAGGATT-TACAGGAGGAGAT-3'" (SEQ ID NO. 13) for coleopteran, lepidopteran, mite, and dipteran-active endotoxin genes;

(iii) a peptide sequence whose single letter amino acid designation is "5'-(A or E)(S or G)(K or E or V)LK(P or R or A or E)(N or Y or F)(T or N)RY-3'" (SEQ ID NO. 14) or variations thereof whose corresponding nucleotide sequence specifies the following universal nucleotide probes: "5'-TAACGTGTAT(A or T)CG(C or G)TTTAATTT(T or A)GA(C or T)TC-3'" (SEQ ID NO. 15) or "5'-GAATCAAAAT-TAAAAGC(A or C)(A or T)ATAC(A or C)(A or C)G(A or C or T)TA-3'" (SEQ ID NO. 16) for nematode, lepidopteran, dipteran, mite, ant, and coleopteran-active endotoxin genes. These genes would specifically code for proteins of approximately 130 kDa;

(iv) a peptide sequence whose single letter amino acid designation is "AKRLS(K or R or D or G or Y)(A or E or I or S)RNLLQDP" (SEQ ID NO. 17) or variations thereof whose corresponding nucleotide sequence specifies the following universal nucleotide probes: "5'-ATTTCGCTCTTTACT(G or A)AGT(C or T)G(C or T)TT(C or T)GC-3'" (SEQ ID NO. 18); "5'-TTCGTGCTTTGCTCAAA(G or C)(G or C)(G or T)(C or T)TTG-3'" (SEQ ID NO. 19); "5'-TGGATCTTGAAGTAAATTCCGTTCAT-CACT(G or A)AGTCG(T or C)TT(T or C)GC-3'" (SEQ ID NO. 20); or "5'-GCGAAGC-GACT(T or C)AGTGATGA(G or A)C-GGAATTTACTTCAAGA(C or T)(C or T)CA-3'" (SEQ ID NO. 21) for nematode, lepidopteran, coleopteran, ant, and dipteran-active endotoxin genes. These genes would typically code for proteins of approximately 130 kDa;

(v) a peptide sequence whose single letter amino acid designation is "GP(G or R)(F or H)(T or I)GG(D or N)" (SEQ ID NO. 22) or variation thereof whose corresponding nucleotide sequence specifies the following universal nucleotide probes: "5'-CCTCCTGTAAATC(T or C)(A or T)GG(A or G or T)CC-3'" (SEQ ID NO. 23) or "5'-GGAC-CAGGATTTACAGG(T or A)GG(A or G)(A or G)A-3'" (SEQ ID NO. 24) for lepidopteran, coleopteran, mite, and dipteran-active endotoxin genes;

(vi) a peptide sequence whose single letter amino acid designation is "LGPLLGFVVYEI" (SEQ ID NO. 25) or variation thereof whose corresponding nucleotide sequences specifies the following sub-universal nucleotide probes: "5'-TTAGGAC-CATT(A or G)(C or T)T(T or A)G-GATTTGTTGT(A or T)TATGAAAT-3'" (SEQ ID NO. 26) for nematode or coleopteran-active endotoxin genes;

(vii) the universal nucleotide probe "5'-CNCCTGCAA(T or C)TCA(T or A)(C or T)A(A or T)A-3'" (SEQ ID NO. 27) for lepidopteran, coleopteran, nematode, and dipteran genes;

(viii) a peptide sequence whose single letter amino acid designation is "DRDVKILGM" (SEQ ID NO. 28) or "DRDVKIIGM" (SEQ ID NO. 29) or a variation thereof whose corresponding nucleotide sequence specifies the following sub-universal nucleotide probes: "5'-GA(C or T)AGAGATG-T(A or T)AAAAT(C or T)(T or A)TAG-GAATG" (SEQ ID NO. 30) for nematode or coleopteran-active endotoxin genes;

(ix) a peptide sequence whose single letter amino acid designation is "DDFNQLYKVY" (SEQ ID NO. 31) or variations thereof which embody point mutations according to the following: position 1, D or S; position 4, N or S; position 8, K or D; and whose corresponding nucleotide sequence specifies the following sub-universal nucleotide probe: "5'-TGATTTT(T or A)(C or A)TCAATTATAT(A or G)A(G or T)GTTTAT-3'+ (SEQ ID NO. 32) for nematode or coleopteran-active endotoxin genes;

(x) a peptide sequence whose single letter amino acid designation is "VLKTANDI" (SEQ ID NO. 33) or variations thereof which embody point mutations according to the following: position 1, V or I; position 2, L or I; position 4, T or S; and whose corresponding nucleotide sequence specifies the following sub-universal nucleotide probes: "5'TT(A or C)TTAAA(A or T)C(A or T)GCTAATGATATT-3'" (SEQ ID NO. 34) for nematode or coleopteran-active endotoxin genes;

(xi) a peptide sequence whose single letter amino acid designation is "EELLEKV" (SEQ ID NO. 35) or variations thereof which embody point mutations according to the following: position 1, E or K; position 5, E or K; and whose corresponding nucleotide sequence specifies the following sub-universal nucleotide probes: "5'-AAGAGTTA(C or T)TA(A or G)A(G or A)AAAGTA-3'" (SEQ ID NO. 36) for nematode or coleopteran-active endotoxin genes;

(xii) a peptide sequence whose single letter amino acid designation is "MIHAAD" (SEQ ID NO. 37) and whose nucleotide sequence specifies the sub-universal nucleotide probes "5'-ATGATT-CATGCGGCAGATA-3'" (SEQ ID NO. 38) or "5'-TATCTGCCGCATGAATCAT-3'" (SEQ ID NO. 39) for coleopteran and lepidopteran-active endotoxin genes;

(xiii) a peptide sequence whose single letter amino acid designation is "WEADPTNP" (SEQ ID NO. 40); "DWEADLNNAQLR" (SEQ ID NO. 41); or variation thereof; whose corresponding nucleotide sequence specifies the following group-specific nucleotide probes: "5'-GAGTGGGAAG-CAGATCTTAATAATGCACAATTAAGG-3'" (SEQ ID NO. 42), "5'-TGGGAAG(A or C)GGATCCTA(A or C)TAATCCA-3'" (SEQ ID NO. 43) for lepidopteran-active endotoxin genes, and which comprise internal sites for cloning PCR DNA (which sites are underlined above);

(xiv) a peptide sequence whose single letter amino acid designation is "TDYHIDQVSNLV" (SEQ ID NO. 44) or variation thereof whose corresponding nucleotide sequence specifies the following sub-universal nucleotide probes: "5'-ATAC(C or T)CGATCGATATGATA(G or A)TCCGT-3'" (SEQ ID NO. 45), "5'-CTAAATTGGATACT-CGATCGATATGATA-3'" (SEQ ID NO. 46), "5'-TATCATATCGATCGAGTATCCAATT-TAG-3'" (SEQ ID NO. 47) for coleopteran and lepidopteran-active endotoxin genes, and which comprise internal sites for cloning PCR DNA (which sites are underlined above);

(xv) a peptide sequence whose single letter amino acid designation is "GDFTQGVMGWH" (SEQ ID NO. 48) and whose nucleotide sequence specifies the group-specific nucleotide probe "5'-GGTGATTTTACACAAGGG-GTAATGGGGTGGCATG" (SEQ ID NO. 49) 3' for dipteran-active endotoxin genes;

(xvi) a peptide sequence whose single letter amino acid designation is "KSKAIAELQG" (SEQ ID NO. 50) and whose nucleotide sequence specifies the group-specific nucleotide probe "5'-AAAGCTCTTGCAGAGTTACAGGG" (SEQ ID NO. 51) 3' for coleopteran-active endotoxin genes;

(xvii) a peptide sequence whose single letter amino acid designation is "RNLLQDP" (SEQ ID NO. 52) or variation thereof whose corresponding nucleotide sequence specifies the following sub-universal nucleotide probes: 5'-TGGATCT(A or T)G(G or A or T)AGTAA(G or A)TT(T or A)C" (SEQ ID NO. 53) 3' or "5'-G(A or T)TT(C or T)TTACT(C or T or A)C(T or A)AGATCCA-3'" (SEQ ID NO. 54) for mite, ant, coleopteran, and lepidopteran-active endotoxin genes. These genes would typically code for proteins of approximately 130 kDa;

(xviii) a peptide sequence whose single letter amino acid designation is "DSIDQLPP" (SEQ ID NO. 55) or variation thereof whose corresponding nucleotide sequence specifies the following sub-universal nucleotide probes: "5'-GATTCCATT-GA(T or C)CAATT(G or A)CC(C or T or A)CC" (SEQ ID NO. 56) 3' for lepidopteran and coleopteran-active endotoxin genes;

(xix) a peptide whose single letter amino acid designation is "LT(I or L)(S or T)VLDI" (SEQ ID NO. 57) or a variation thereof whose corresponding nucleotide sequences specifies the following group-specific nucleotide probes: "5'-TTAACA(C or A)T(T or G)(A or T)C(T or A)GTAT-TAGATAT-3'" (SEQ ID NO. 58) for lepidopteran-active endotoxin genes;

(xx) a peptide sequence whose single letter amino acid designation is "REWINGAN" (SEQ ID NO. 59) or variations thereof which embody point mutations according to the following: position 1, R or P or K; position 3, W or Y; position 4,I or L; position 8, N or Q; and whose corresponding nucleotide sequence specifies the following group-specific nucleotide probes: "5'-AGA(A or G)T(G or A)(G or T)(A or T)T(A or T)AATGG(A or T)GC(G or T)(A or C)A(A or T)-3'" (SEQ ID NO. 60) for nematode-active endotoxin genes;

(xxi) a peptide sequence whose single letter amino acid designation is "PTFDPDLY" (SEQ ID NO. 61) or variations thereof which embody point mutations according to the following: position 3, F or L; position 4, D or Y; position 7, L or H or D; and whose corresponding nucleotide sequence specifies the following universal nucleotide probes: "5'-CC(A or T)AC(C or T)TTT(T or G)ATC-CAGAT(C or G)(T or A)(T or C)TAT-3'" (SEQ ID NO. 62) for ant, coleopteran, mite, lepidopteran, and nematode-active endotoxin genes;

(xxii) A set of peptide sequences whose single letter amino acid designations are "RIILGSGP" (SEQ ID NO. 63), "SPIGKCAH" (SEQ ID NO. 64), "PIHFPST" (SEQ ID NO. 65), "AEELPIRG-GEL" (SEQ ID NO. 66), "NVMESSA" (SEQ ID NO. 67), "VSASTVQTG" (SEQ ID NO. 68), "HVYTNHCVDT" (SEQ ID NO. 69), and "VAAEIGLG" (SEQ ID NO. 70) whose nucleotide sequences specify, respectively, the gene-specific nucleotide probes "5'-GAAT-TATACTTGGTTCAGGCCC-3'" (SEQ ID NO. 71), "5'-GTCCAATCGGAAAATGTGCCC-3'" (SEQ ID NO. 72), "5'-CCAATTCACTTC-CCATCGAC-3'" (SEQ ID NO. 73), "5'-GCTGAAGAACTTCCTATTCGTGGTGGT-GAGC-3'" (SEQ ID NO. 74), "5'-CGTTATG-GAGAGCAGCGCA-3'" (SEQ ID NO. 75), "5'-GTTAGCGCATCAACAGTCCAAACGGG-3'" (SEQ ID NO. 76), "5'-CATGTTTATAC-TAACCATTGTGTGGATACG-3'" (SEQ ID NO. 77), and "5'-CGTAGCAG-CAGAAATCGGCTTGGGC-3'" (SEQ ID NO. 78) for lepidopteran-active endotoxin genes;

(xxiii) A set of peptide sequences whose single letter amino acid designations are "GGTNMNPI" (SEQ ID NO. 79), and "GYPLANDLQG" (SEQ ID NO. 80) whose nucleotide sequences specify, respectively, the gene-specific nucleotide probes "5'-GGGAGGAACAAATATGAATCCT-TATC-3'" (SEQ ID NO. 81), and "5'-CAGG-CTATCCGTTAGCGAATGACT-TACAAGGG-3'" (SEQ ID NO. 82) for dipteran-active endotoxin genes;

(xxiv) A set of peptide sequences whose single letter amino acid designations are "NVGAVSW" (SEQ ID NO. 83), and "YNGYLGAQ" (SEQ ID NO. 84) whose nucleotide sequences specify, respectively, the gene-specific nucleotide probes "5'-AATGTTGGCGCGGTCAGCTGGG-3'" (SEQ ID NO. 85), "5'-TACAATGGCTATTTAGGT-GCACAG-3'" (SEQ ID NO. 86) for coleopteran-active endotoxin genes; and (xxv) A peptide sequence whose single letter amino acid designation is "I(T or S)SEDGE" (SEQ ID NO. 87) whose nucleotide sequences specify the sub-universal nucleotide probes "5'-ATT(T or A)C(T or C)TCAGAAGATGGAGA-3'" (SEQ ID NO. 88) and "5'-TCTCCATCTTCTGA(G or A)G(A or T)AA-3'" (SEQ ID NO. 89) for nematode, coleopteran, mite, ant, and lepidopteran-active endotoxin genes.

In one embodiment of the subject invention, a B.t. isolate suspected of containing a gene of interest may be used directly or cultivated under conditions where clones are grown providing high multiplication of the organism of interest. After treating the genome to provide single stranded genomic nucleic acid and fixing the nucleic acid to a support, the affixed DNA or RNA can be contacted with a labeled polynucleotide sequence of the subject invention.

A primary feature of the subject invention is the use of labeled probes. The probe may be RNA or DNA. The probe will normally have at least about 10 bases, more usually at least about 18 bases, and may have up to about 50 bases or more, usually not having more than about 200 bases if the probe is made synthetically. However, longer probes can readily be utilized, and such probes can be prepared using, for example, standard PCR techniques. These probes can be, for example, several kilobases in length. The probe sequence is designed to be at least substantially complementary to a gene coding for a toxin of interest. The probe need not have perfect complementarity to the sequence to which it hybridizes.

Another important aspect of the subject invention is the use of the nucleotide sequences of the subject invention as primers in PCR techniques. As described in detail below, these primers can be used to produce gene fragments which are characteristic of the particular biological activity of a given gene.

BRIEF DESCRIPTION OF THE DRAWINGS

FIG. 1 shows an autoradiogram of 66 different *Bacillus thuringiensis* isolates all positively hybridizing with the universal nucleotide probe GGACCAGGATTACAGGAGGAGAT (SEQ ID NO. 13).

FIG. 2 shows an autoradiogram of the same 66 different *Bacillus thuringiensis* isolates as in FIG. 1, but this time probed with the "AEELPIRGGEL" (SEQ ID NO. 66) gene-specific probe.

BRIEF DESCRIPTION OF THE SEQUENCES

SEQ ID NO. 1 is a peptide sequence designating universal nucleotide probes according to the subject invention.

SEQ ID NO. 2 is a universal nucleotide probe according to the subject invention, encoding the peptide sequence of SEQ ID NO. 1.

SEQ ID NO. 3 is a universal nucleotide probe according to the subject invention, encoding the peptide sequence of SEQ ID NO. 1.

SEQ ID NO. 4 is a universal nucleotide probe according to the subject invention, encoding the peptide sequence of SEQ ID NO. 1.

SEQ ID NO. 5 is a universal nucleotide probe according to the subject invention, encoding the peptide sequence of SEQ ID NO. 1.

SEQ ID NO. 6 is a universal nucleotide probe according to the subject invention, encoding the peptide sequence of SEQ ID NO. 1.

SEQ ID NO. 7 is a universal nucleotide probe according to the subject invention, encoding the peptide sequence of SEQ ID NO. 1.

SEQ ID NO. 8 is a universal nucleotide probe according to the subject invention, encoding the peptide sequence of SEQ ID NO. 1.

SEQ ID NO. 9 is a universal nucleotide probe according to the subject invention, encoding the peptide sequence of SEQ ID NO. 1.

SEQ ID NO. 10 is a universal nucleotide probe according to the subject invention, encoding the peptide sequence of SEQ ID NO. 1.

SEQ ID NO. 11 is a universal nucleotide probe according to the subject invention, encoding the peptide sequence of SEQ ID NO. 1.

SEQ ID NO. 12 is a peptide sequence designating a universal nucleotide probe according to the subject invention.

SEQ ID NO. 13 is a universal nucleotide probe according to the subject invention, encoding the peptide sequence of SEQ ID NO. 12.

SEQ ID NO. 14 is a peptide sequence designating universal nucleotide probes according to the subject invention.

SEQ ID NO. 15 is a universal nucleotide probe according to the subject invention, encoding the peptide sequence of SEQ ID NO. 14.

SEQ ID NO. 16 is a universal nucleotide probe according to the subject invention, encoding the peptide sequence of SEQ ID NO. 14.

SEQ ID NO. 17 is a peptide sequence designating universal nucleotide probes according to the subject invention.

SEQ ID NO. 18 is a universal nucleotide probe according to the subject invention, encoding the peptide sequence of SEQ ID NO. 17.

SEQ ID NO. 19 is a universal nucleotide probe according to the subject invention, encoding the peptide sequence of SEQ ID NO. 17.

SEQ ID NO. 20 is a universal nucleotide probe according to the subject invention, encoding the peptide sequence of SEQ ID NO. 17.

SEQ ID NO. 21 is a universal nucleotide probe according to the subject invention, encoding the peptide sequence of SEQ ID NO. 17.

SEQ ID NO. 22 is a peptide sequence designating universal nucleotide probes according to the subject invention.

SEQ ID NO. 23 is a universal nucleotide probe according to the subject invention, encoding the peptide sequence of SEQ ID NO. 22.

SEQ ID NO. 24 is a universal nucleotide probe according to the subject invention, encoding the peptide sequence of SEQ ID NO. 22.

SEQ ID NO. 25 is a peptide sequence designating sub-universal nucleotide probes according to the subject invention.

SEQ ID NO. 26 is a sub-universal nucleotide probe according to the subject invention, encoding the peptide sequence of SEQ ID NO. 25.

SEQ ID NO. 27 is a universal probe according to the subject invention.

SEQ ID NO. 28 is a peptide sequence designating sub-universal nucleotide probes according to the subject invention.

SEQ ID NO. 29 is a peptide sequence designating sub-universal nucleotide probes according to the subject invention.

SEQ ID NO. 30 is a sub-universal probe according to the subject invention, encoding the peptide sequence of SEQ ID NOS. 28 or 29.

SEQ ID NO. 31 is a peptide sequence designating a sub-universal nucleotide probes according to the subject invention.

SEQ ID NO. 32 is a sub-universal probe according to the subject invention, encoding the peptide sequence of SEQ ID NO. 31.

SEQ ID NO. 33 is a peptide sequence designating sub-universal nucleotide probes according to the subject invention.

SEQ ID NO. 34 is a sub-universal probe according to the subject invention, encoding the peptide sequence of SEQ ID NO. 33.

SEQ ID NO. 35 is a peptide sequence designating sub-universal nucleotide probes according to the subject invention.

SEQ ID NO. 36 is a sub-universal probe according to the subject invention, encoding the peptide sequence of SEQ ID NO. 35.

SEQ ID NO. 37 is a peptide sequence designating group-specific nucleotide probes according to the subject invention.

SEQ ID NO. 38 is a sub-universal probe according to the subject invention, encoding the peptide sequence of SEQ ID NO. 36.

SEQ ID NO. 39 is a sub-universal probe according to the subject invention, encoding the peptide sequence of SEQ ID NO. 36.

SEQ ID NO. 40 is a peptide sequence designating group-specific nucleotide probes according to the subject invention.

SEQ ID NO. 41 is a peptide sequence designating group-specific nucleotide probes according to the subject invention.

SEQ ID NO. 42 is a group-specific probe according to the subject invention, encoding the peptide sequence of SEQ ID NOS. 40 or 41.

SEQ ID NO. 43 is a group-specific probe according to the subject invention, encoding the peptide sequence of SEQ ID NOS. 40 or 41.

SEQ ID NO. 44 is a 2peptide sequence designating group-specific nucleotide probes according to the subject invention.

SEQ ID NO. 45 is a sub-universal probe according to the subject invention, encoding the peptide sequence of SEQ ID NO. 44.

SEQ ID NO. 46 is a sub-universal probe according to the subject invention, encoding the peptide sequence of SEQ ID NO. 44.

SEQ ID NO. 47 is a sub-universal probe according to the subject invention, encoding the peptide sequence of SEQ ID NO. 44.

SEQ ID NO. 48 is a peptide sequence designating group-specific nucleotide probes according to the subject invention.

SEQ ID NO. 49 is a group-specific probe according to the subject invention, encoding the peptide sequence of SEQ ID NO. 48.

SEQ ID NO. 50 is a peptide sequence designating group-specific nucleotide probes according to the subject invention.

SEQ ID NO. 51 is a group-specific probe according to the subject invention, encoding the peptide sequence of SEQ ID NO. 50.

SEQ ID NO. 52 is a peptide sequence designating group-specific nucleotide probes according to the subject invention.

SEQ ID NO. 53 is a sub-universal probe according to the subject invention, encoding the peptide sequence of SEQ ID NO. 52.

SEQ ID NO. 54 is a sub-universal probe according to the subject invention, encoding the peptide sequence of SEQ ID NO. 52.

SEQ ID NO. 55 is a peptide sequence designating sub-universal nucleotide probes according to the subject invention.

SEQ ID NO. 56 is a sub-universal probe according to the subject invention, encoding the peptide sequence of SEQ ID NO. 55.

SEQ ID NO. 57 is a peptide sequence designating group-specific nucleotide probes according to the subject invention.

SEQ ID NO. 58 is a group-specific probe according to the subject invention, encoding the peptide sequence of SEQ ID NO. 57.

SEQ ID NO. 59 is a peptide sequence designating group-specific nucleotide probes according to the subject invention.

SEQ ID NO. 60 is a group-specific probe according to the subject invention, encoding the peptide sequence of SEQ ID NO. 59.

SEQ ID NO. 61 is a peptide sequence designating group-specific nucleotide probes according to the subject invention.

SEQ ID NO. 62 is a universal probe according to the subject invention, encoding the peptide sequence of SEQ ID NO. 61.

SEQ ID NO. 63 is one of a set of peptide sequences designating gene-specific nucleotide probes for lepidopteran-active endotoxin genes according to the subject invention.

SEQ ID NO. 64 is one of a set of peptide sequences designating gene-specific nucleotide probes for lepidopteran-active endotoxin genes according to the subject invention.

SEQ ID NO. 65 is one of a set of peptide sequences designating gene-specific nucleotide probes for lepidopteran-active endotoxin genes according to the subject invention.

SEQ ID NO. 66 is one of a set of peptide sequences designating gene-specific nucleotide probes for lepidopteran-active endotoxin genes according to the subject invention.

SEQ ID NO. 67 is one of a set of peptide sequences designating gene-specific nucleotide probes for lepidopteran-active endotoxin genes according to the subject invention.

SEQ ID NO. 68 is one of a set of peptide sequences designating gene-specific nucleotide probes for lepidopteran-active endotoxin genes according to the subject invention.

SEQ ID NO. 69 is one of a set of peptide sequences designating gene-specific nucleotide probes for lepidopteran-active endotoxin genes according to the subject invention.

SEQ ID NO. 70 is one of a set of peptide sequences designating gene-specific nucleotide probes for lepidopteran-active endotoxin genes according to the subject invention.

SEQ ID NO. 71 is a gene-specific nucleotide probe encoding the peptide sequence of SEQ ID NO. 63.

SEQ ID NO. 72 is a gene-specific nucleotide probe encoding the peptide sequence of SEQ ID NO. 64.

SEQ ID NO. 73 is a gene-specific nucleotide probe encoding the peptide sequence of SEQ ID NO. 65.

SEQ ID NO. 74 is a gene-specific nucleotide probe encoding the peptide sequence of SEQ ID NO. 66.

SEQ ID NO. 75 is a gene-specific nucleotide probe encoding the peptide sequence of SEQ ID NO. 67.

SEQ ID NO. 76 is a gene-specific nucleotide probe encoding the peptide sequence of SEQ ID NO. 68.

SEQ ID NO. 77 is a gene-specific nucleotide probe encoding the peptide sequence of SEQ ID NO. 69.

SEQ ID NO. 78 is a gene-specific nucleotide probe encoding the peptide sequence of SEQ ID NO. 70.

SEQ ID NO. 79 is one of a set of peptide sequences designating gene-specific nucleotide probes for dipteran-active endotoxin genes according to the subject invention.

SEQ ID NO. 80 is one of a set of peptide sequences designating gene-specific nucleotide probes for dipteran-active endotoxin genes according to the subject invention.

SEQ ID NO. 81 is a gene-specific nucleotide probe encoding the peptide sequence of SEQ ID NO. 79.

SEQ ID NO. 82 is a gene-specific nucleotide probe encoding the peptide sequence of SEQ ID NO. 80.

SEQ ID NO. 83 is one of a set of peptide sequences designating gene-specific nucleotide probes for coleopteran-active endotoxin genes according to the subject invention.

SEQ ID NO. 84 is one of a set of peptide sequences designating gene-specific nucleotide probes for coleopteran-active endotoxin genes according to the subject invention.

SEQ ID NO. 85 is a gene-specific nucleotide probe encoding the peptide sequence of SEQ ID NO. 83.

SEQ ID NO. 86 is a gene-specific nucleotide probe encoding the peptide sequence of SEQ ID NO. 84.

SEQ ID NO. 87 is a peptide sequence designating sub-universal nucleotide probes according to the subject invention.

SEQ ID NO. 88 is a sub-universal probe according to the subject invention, encoding the peptide sequence of SEQ ID NO. 87.

SEQ ID NO. 89 is a sub-universal probe according to the subject invention, encoding the peptide sequence of SEQ ID NO. 87.

DETAILED DISCLOSURE OF THE INVENTION

The subject invention concerns DNA or RNA probes and primers for identifying B.t. nucleotide sequences which encode protein toxins which are active against various pests.

It is well known that DNA possesses a fundamental property called base complementarity. In nature, DNA ordinarily exists in the form of pairs of anti-parallel strands, the bases on each strand projecting from that strand toward the opposite strand. The base adenine (A) on one strand will always be opposed to the base thymine (T) on the other strand, and the base guanine (G) will be opposed to the base cytosine (C). The bases are held in apposition by their ability to hydrogen bond in this specific way. Though each individual bond is relatively weak, the net effect of many adjacent hydrogen bonded bases, together with base stacking effects, is a stable joining of the two complementary strands. These bonds can be broken by treatments such as high pH or high temperature, and these conditions result in the dissociation, or "denaturation," of the two strands. If the DNA is then placed in conditions which make hydrogen bonding of the bases thermodynamically favorable, the DNA strands will anneal, or "hybridize," and reform the original double stranded DNA. If carried out under appropriate conditions, this hybridization can be highly specific. That is, only strands with a high degree of base complementarity will be able to form stable double stranded structures. The relationship of the specificity of hybridization to reaction conditions is well known. Thus, hybridization may be used to test whether two pieces of DNA are complementary in their base sequences. It is this hybridization mechanism which facilitates the use of probes of the subject invention to readily detect and characterize DNA sequences of interest.

The probes of the subject invention have been categorized as "universal," "sub-universal," "group-specific," or "gene-specific" depending upon the range of B.t. toxin genes with which the probe will hybridize. For example, as used herein, "universal probes" refer to those probes which hybridize with a variety of B.t. genes coding for different B.t. toxins having activity against different pests. As defined herein, a "universal probe" hybridizes with at least three different genes coding for toxins having activity against different pests (or, perhaps, a single gene with multiple pesticidal activities). For example, the universal probe designated (ii) hybridizes with genes coding for coleopteran-active toxins, genes coding for lepidopteran-active toxins, and genes coding for dipteran-active toxins. Because the "universal probes" hybridize with a variety of different B.t. genes, these probes can be used to initially screen B.t. DNA to determine if any of a broad range of B.t. genes are present.

The probes which have been designated herein as "sub-universal" are known to hybridize with a range of B.t. genes which is smaller than the range with which the universal probes hybridize. Specifically, the sub-universal probes hybridize with different genes coding for toxins having activity against two different pests. For example, the sub-universal probes designated in part (vii) above hybridize with genes coding for nematode-active toxins and genes coding for coleopteran-active toxins.

"Group-specific probes" are more specific than universal or sub-universal probes and hybridize only with genes coding for toxins active against a certain pest. For example, the probe shown in part (xii) above hybridizes with genes coding for toxins active against lepidopterans.

The most specific probes described herein are the "gene-specific" probes which hybridize to a small number of genes which would all code for toxins active against the same pest. Probes described in (xxii) to (xxiii) above provide examples of these specific probes.

In order to analyze B.t. DNA according to the subject invention, the DNA can first be obtained in its native, double-stranded form. A number of procedures are currently used to isolate DNA and are well known to those skilled in this art.

One approach for the use of the invention probes entails first identifying by Southern blot analysis of a gene bank of the B.t. isolate all DNA segments homologous with a universal or sub-universal probe. Subsequently, nematode, lepidopteran, coleopteran, and dipteran-active gene segments can be identified with a similar analysis using each of the group-specific probes. The specific nature of each of the gene segments can be probed further using the sets of specific probes for nematode, lepidopteran, coleopteran, and dipteran-active genes listed above. Thus, it is possible, without the aid of biological analysis, to know in advance the probable activity of many new B.t. isolates, and of the individual endotoxin gene products expressed by a given B.t. isolate. Such a probe analysis provides a rapid method for identifying potentially commercially valuable insecticidal endotoxin genes within the multifarious subspecies of B.t.

One hybridization procedure useful according to the subject invention typically includes the initial steps of isolating the DNA sample of interest and purifying it chemically. Either lysed bacteria or total fractionated nucleic acid isolated from bacteria can be used. Cells can be treated using known techniques to liberate their DNA (and/or RNA). The DNA sample can be cut into pieces with an appropriate restriction enzyme. The pieces can be separated by size through electrophoresis in a gel, usually agarose or acrylamide. The pieces of interest can be transferred to an immobilizing membrane in a manner that retains the geometry of the pieces. The membrane can then be dried and prehybridized to equilibrate it for later immersion in a hybridization solution. The manner in which the nucleic acid is affixed to a solid support may vary. This fixing of the DNA for later processing has great value for the use of this technique in field studies, remote from laboratory facilities.

The particular hybridization technique is not essential to the subject invention. As improvements are made in hybridization techniques, they can be readily applied.

As is well known in the art, if the probe molecule and nucleic acid sample hybridize by forming a strong non-covalent bond between the two molecules, it can be reasonably assumed that the probe and sample are essentially identical. The probe's detectable label provides a means for determining in a known manner whether hybridization has occurred.

The nucleotide segments which are used as probes according to the invention can be synthesized by use of DNA synthesizers using standard procedures. In the use of the nucleotide segments as probes, the particular probe is labeled with any suitable label known to those skilled in the art, including radioactive and non-radioactive labels. Typical radioactive labels include $^{32}P$, $^{35}S$, or the like. A probe labeled with a radioactive isotope can be constructed from a nucleotide sequence complementary to the DNA sample by a conventional nick translation reaction, using a DNase and DNA polymerase. The probe and sample can then be combined in a hybridization buffer solution and held at an appropriate temperature until annealing occurs. Thereafter, the membrane is washed free of extraneous materials, leaving the sample and bound probe molecules typically detected and quantified by autoradiography and/or liquid scintillation counting. For synthetic probes, it may be most desirable to use enzymes such as polynucleotide kinase or terminal transferase to end-label the DNA for use as probes.

Non-radioactive labels include, for example, ligands such as biotin or thyroxine, as well as enzymes such as hydrolases or perixodases, or the various chemiluminescers such as luciferin, or fluorescent compounds like fluorescein and its derivatives. The probe may also be labeled at both ends with different types of labels for ease of separation, as, for example, by using an isotopic label at the end mentioned above and a biotin label at the other end.

The amount of labeled probe which is present in the hybridization solution will vary widely, depending upon the nature of the label, the amount of the labeled probe which can reasonably bind to the filter, and the stringency of the hybridization. Generally, substantial excesses over stoichiometric of the probe will be employed to enhance the rate of binding of the probe to the fixed DNA.

Various degrees of stringency of hybridization can be employed. The more severe the conditions, the greater the complementarity that is required for duplex formation. Severity can be controlled by temperature, probe concentration, probe length, ionic strength, time, and the like.

Duplex formation and stability depend on substantial complementarity between the two strands of a hybrid, and, as noted above, a certain degree of mismatch can be tolerated. Therefore, the probes of the subject invention include mutations (both single and multiple), deletions, insertions of the described sequences, and combinations thereof, wherein said mutations, insertions and deletions permit formation of stable hybrids with the target polynucleotide of interest. Mutations, insertions, and deletions can be produced in a given polynucleotide sequence in many ways, and these methods are known to an ordinarily skilled artisan. Other methods may become known in the future.

The known methods include, but are not limited to:
(1) synthesizing chemically or otherwise an artificial sequence which is a mutation, insertion or deletion of the known sequence;
(2) using a probe of the present invention to obtain via hybridization a new sequence or a mutation, insertion or deletion of the probe sequence; and
(3) mutating, inserting or deleting a test sequence in vitro or in vivo.

It is important to note that the mutational, insertional, and deletional variants generated from a given probe may be more or less efficient than the original probe. Notwithstanding such differences in efficiency, these variants are within the scope of the present invention.

Thus, mutational, insertional, and deletional variants of the disclosed test sequences can be readily prepared by methods which are well known to those skilled in the art. These variants can be used in the same manner as the instant probes so long as the variants have substantial sequence homology with the probes. As used herein, substantial sequence homology refers to homology which is sufficient to enable the variant to function in the same capacity as the original probe. Preferably, this homology is greater than 50%; more preferably, this homology is greater than 75%; and most preferably, this homology is greater than 90%. The degree of homology needed for the variant to function in its intended capacity will depend upon the intended use of the sequence. It is well within the skill of a person trained in this art to make mutational, insertional, and deletional mutations which are designed to improve the function of the sequence or otherwise provide a methodological advantage.

It is well known in the art that the amino acid sequence of a protein is determined by the nucleotide sequence of the DNA. Because of the redundancy of the genetic code, i.e., more than one coding nucleotide triplet (codon) can be used for most of the amino acids used to make proteins, different nucleotide sequences can code for a particular amino acid. Thus, the genetic code can be depicted as follows:

| Phenylalanine (Phe) | TTK | Histidine (His) | CAK |
|---|---|---|---|
| Leucine (Leu) | XTY | Glutamine (Gln) | CAJ |
| Isoleucine (Ile) | ATM | Asparagine (Asn) | AAK |
| Methionine (Met) | ATG | Lysine (Lys) | AAJ |
| Valine (Val) | GTL | Aspartic acid (Asp) | GAK |
| Serine (Ser) | QRS | Glutamic acid (Glu) | GAJ |
| Proline (Pro) | CCL | Cysteine (Cys) | TGK |
| Threonine (Thr) | ACL | Tryptophan (Trp) | TGG |
| Alanine (Ala) | GCL | Arginine (Arg) | WGZ |
| Tyrosine (Tyr) | TAK | Glycine (Gly) | GGL |
| Termination signal | TAJ | Termination signal | TGA |

Key: Each 3-letter deoxynucleotide triplet corresponds to a trinucleotide of mRNA, having a 5'-end on the left and a 3'-end on the right. All DNA sequences given herein are those of the strand whose sequence correspond to the mRNA sequence, with thymine substituted for uracil. The letters stand for the purine or pyrimidine bases forming the deoxynucleotide sequence.

```
A = adenine
G = guanine
C = cytosine
T = thymine
X = T or C if Y is A or G
X = C if Y is C or T
Y = A, G, C or T if X is C
Y = A or G if X is T
W = C or A if Z is A or G
W — C if Z is C or T
Z = A, G, C or T if W is C
Z = A or G if W is A
QR = TC if S is A, G, C or T; alternatively
QR = AG if S is T or C
J = A or G
K = T or C
L = A, T, C or G
M = A, C or T
```

The above shows that the amino acid sequence of B.t. toxins can be encoded by equivalent nucleotide sequences encoding the same amino acid sequence of the protein. Accordingly, the subject invention includes probes which would hybridize with various polynucleotide sequences which would all code for a given protein or variations of a given protein. In addition, it has been shown that proteins of identified structure and function may be constructed by changing the amino acid sequence if such changes do not alter the protein secondary structure (Kaiser, E. T., Kezdy, F. J. [1984] *Science* 223:249–255).

A preferred method for synthesizing nucleic acids is based on repetitive, enzymatic, primed synthesis of a nucleic acid sequence, also known as Polymerase Chain Reaction ("PCR") (see U.S. Pat. No. 4,683,195). This procedure is well known and commonly used by those skilled in this art. PCR is based on the enzymatic amplification of a DNA fragment of interest that is flanked by two oligonucleotide primers that hybridize to opposite strands of the target sequence. The primers are oriented with the 3' ends pointing towards each other. Repeated cycles of heat denaturation of the template, annealing of the primers to their complementary sequences, and extension of the annealed primers with a DNA polymerase result in the amplification of the segment defined by the 5' ends of the PCR primers. Since the extension product of each primer can serve as a template for the other primer, each cycle essentially doubles the amount of DNA fragment produced in the previous cycle. This results in the exponential accumulation of the specific target fragment, up to several millionfold in a few hours. By using the thermostable Taq DNA polymerase isolated from the thermophilic bacterium *Thermus aquaticus*, the amplification process can be completely automated.

In addition to their use as probes, the DNA sequences of the subject invention can be used as primers for PCR amplification. In performing PCR amplification, a certain degree of mismatch can be tolerated between primer and template. Therefore, mutations, deletions, and insertions (especially additions of nucleotides to the 5' end) of the exemplified primers fall within the scope of the subject invention. Mutations, insertions and deletions can be produced in a given primer by methods known to an ordinarily skilled artisan. It is important to note that the mutational, insertional, and deletional variants generated from a given primer sequence may be more or less efficient than the original sequences. Notwithstanding such differences in efficiency, these variants are within the scope of the present invention.

In addition, PCR-amplified DNA may serve as a hybridization probe. Alternately, it may be sequenced directly, or after cloning into a suitable vector. Derived sequence from PCR DNA may be used to design and construct additional probes.

Following are examples which illustrate procedures, including the best mode, for practicing the invention. These examples should not be construed as limiting. All percentages are by weight and all solvent mixture proportions are by volume unless otherwise noted.

EXAMPLE 1

Rapid Genetic Characterization of Bacterial Soil Isolates Using Oligonucleotide Probe Hybridization to Colony (Dot) Blots The dot blot method for characterizing toxin genes in *Bacillus thuringiensis* or any bacterial soil isolate was developed because of the evolution of an oligonucleotide probe library. This library is an aspect of the subject invention. The assay procedure involves growing liquid bacterial culture from a sporulated colony and filtering it through a nylon membrane on a dot blot apparatus to collect the cells. The cells are protoplasted by exposing the membrane to 3 mm paper soaked in a solution containing 30 mg/ml lysozyme to a final pH of 8.0 for 20 minutes. This treatment is followed by a 10 minute treatment with 10% SDS, 5 minutes with 0.5N NaOH, 1.5M NaCl, 5 minutes with 1M Tris-HCl 1.5M NaCl, pH=8.0, and 5 minutes with 2×SSPE (300 mM NaCl, 20 mM $NaH_2PO_4$, 2 mM EDTA, pH=7.4). The membrane is baked in an oven for 2 hours at 80° C. The DNA of each isolate can then be characterized by hybridization with [$^{32}$P]-radiolabeled oligonucleotide probes from the library using standard hybridization and autoradiography techniques. FIGS. 1–2 give an example of the typical results displaying the use of general and specific oligonucleotide probes for genetically characterizing bacterial soil isolates.

EXAMPLE 2

Use of Oligonucleotides as Primers in PCR Procedures

As described above, the probes of the subject invention can be used as primers in standard PCR procedures to obtain genes according to the subject invention. Advantageously, these primers can be used to identify B.t. genes having specific activities. Table 1 shows combinations of forward and reverse primers (Probe Combinations) which can be used to amplify B.t. genes. Table 1 provides the expected fragment sizes for each combination of primers. Amplified DNA fragments of the indicated sizes can be radiolabeled and used as probes to clone the entire gene. Also, the expected activity of the gene products of these genes is provided in Table 1.

The SEQ ID numbers used in Table 1 refer to the peptide sequences used for probe designs. Clearly, the probes themselves are nucleotide sequences. Thus, the probes used are nucleotide sequences which code for the indicated peptide. Predicted sizes of the PCR-amplified DNAs reported in Table 1 have been rounded to the nearest 5 base pairs. As expected, length of the PCR product will vary depending on the length of the primer used. The minimum size of the PCR product may be 10 to 35 base pairs shorter than that shown in the table. It would be reasonable to expect that an actual PCR DNA size for a predicted bioactivity may vary from 10 to 35 base pairs shorter than that shown in the table, or 10 to 50 base pairs larger than that shown in the table, depending on the size of the PCR product (e.g., smaller 100 to 300 bp products may only change by 10 or so base pairs).

TABLE 1

Predicted fragment sizes for probe combinations used in PCR.

| SEQ ID Combination | Size in base pairs | Activity |
|---|---|---|
| 01/14 | 1070, 800, 780, 590 | nematodes |
|  | 1070, 780, 590, 265 | mites |
|  | 590 | ants |
|  | 1070, 780, 590, 445, 265 | coleopterans |
|  | 590, 450, 445, 265 | lepidopterans |
|  | 455 | dipterans |
| 12 or 22/14 | 775 | mites |
|  | 830, 780, 775 | coleopterans |
|  | 830, 810, 780, 775, 760 | lepidopterans |
|  | 835, 890 | dipterans |
| 12 or 22/01 | 345 | mites |
|  | 355, 350, 345 | coleopterans |
|  | 385, 355, 350, 345, 335 | lepidopterans |
|  | 400, 360 | dipterans |
| 44/14 | 370 | coleopterans |
|  | 370, 320 | lepdopterans |
| 44/52 | 135 | coleopterans |
|  | 135 | lepidopterans |
| 44/37 | 930 | coleopterans |
|  | 930, 875, 795 | lepidopterans |
| 44/17 | 120 | coleopterans |
|  | 120 | lepidopterans |
| 01/44 | 150 | coleopterans |
|  | 150 | lepidopterans |
| 01/17 | 250 | coleopterans |
|  | 250, 240 | lepidopterans |
| 01/52 | 265 | mites |
|  | 265 | coleopterans |
|  | 265 | lepidopterans |
| 01/37 | 1060 | coleopterans |
|  | 1060, 1005, 925 | lepidopterans |
| 12 or 22/40 or 41 | 585 | mites |
|  | 600, 595, 585 | coleopterans |
|  | 630, 600, 595, 590, 585, 580 | lepidopterans |
| 12 or 22/37 | 1385 | coleopterans |
|  | 1385, 1340, 1330, 1315, 1255 | lepidopterans |
| 12 or 22/44 | 475 | coleopterans |
|  | 515, 485, 475, 460 | lepidopterans |
| 12 or 22/17 | 580 | coleopterans |
|  | 615, 585, 580, 575, 565 | lepidopterans |
| 52/14 | 210, 180, 155 | coleopterans |
|  | 210, 165, 155 | lepidopterans |
| 14/37 | 585 | coleopterans |
|  | 585, 505 | lepidopterans |
| 17/37 | 835 | coleopterans |
|  | 835, 780, 705 | lepidopterans |
| 17/14 | 205 | nematodes |
|  | 280 | coleopterans |
|  | 280, 225 | lepidopterans |
|  | 220 | dipterans |
| 55/14 | 1025, 1015 | coleopterans |
|  | 1025 | lepidopterans |
| 61/87 | 3120, 2830, 2805, 2650 | nematodes |
|  | 2120, 2830, 2650 | mites |
|  | 2650 | ants |
|  | 3120, 2830, 2650 | coleopterans |
|  | 2650 | lepidopterans |
| 61/14 | 2150, 1865, 1790, 1685 | nematodes |
|  | 2150, 1865, 1685 | mites |
|  | 1685 | ants |
|  | 2150, 1865, 1685 | coleopterans |
|  | 1685 | lepidopterans |
| 61/01 | 1120, 1115, 1110, 1105 | nematodes |
|  | 1115, 1105 | mites |
|  | 1115 | ants |
|  | 1115, 1105 | coleopterans |
|  | 1115 | lepidopterans |
| 61/17 | 1975, 1690, 1615, 1505 | nematodes |
|  | 1975, 1690, 1505 | mites |
|  | 1505 | ants |
|  | 1975, 1690, 1505 | coleopterans |
|  | 1505 | lepidopterans |
| 61/52 | 1030 | nematodes |
|  | 1030 | ants |
| 14/87 | 1045, 995 | nematodes |

TABLE 1-continued

Predicted fragment sizes for probe combinations used in PCR.

| SEQ ID Combination | Size in base pairs | Activity |
| --- | --- | --- |
| | 995 | mites |
| | 995 | ants |
| | 995 | lepidopterans |
| 40/14 | 1925, 1900, 1895, 1880, 1850 | lepidopterans |
| 55/01 | 590, 580,, 575 | coleopterans |
| 55/52 | 835 | coleopterans |
| 17/87 | 1220 | nematodes |
| 40/01 | 1495, 1475, 1470, 1465, 1455, 1450, 1425 | lepidopterans |
| 40/44 | 1625, 1600, 1595, 1580, 1550 | lepidopterans |
| 40/17 | 1725, 1700, 1695, 1685, 1680, 1655 | lepidopterans |
| 40/52 | 1740, 1715, 1710, 1700, 1695, 1670 | lepidopterans |
| 40/37 | 2480, 2455, 2450, 2435, 2405, 2375 | lepidopterans |
| 01/57 | 1100, 1110, 1115, 1140, 1170, 1190, 1195 | lepidopterans |

It should be understood that the examples and embodiments described herein are for illustrative purposes only and that various modifications or changes in light thereof will be suggested to persons skilled in the art and are to be included within the spirit and purview of this application and the scope of the appended claims.

SEQUENCE LISTING ( 1 ) GENERAL INFORMATION:

( i i i ) NUMBER OF SEQUENCES: 89

( 2 ) INFORMATION FOR SEQ ID NO:1:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:1:

Tyr  Ile  Asp  Lys  Ile  Glu  Phe  Ile  Pro
1              5                        9

( 2 ) INFORMATION FOR SEQ ID NO:2:

( i ) SEQUENCE CHARACTERISTICS:
        ( A ) LENGTH: 23 bases
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:2:

TGGAATAAAT TCAATTYKRT CWA                                                         2 3

( 2 ) INFORMATION FOR SEQ ID NO:3:

( i ) SEQUENCE CHARACTERISTICS:
        ( A ) LENGTH: 21 bases
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:3:

TAGAYARAAT TGAATTTAT W C                                                          2 1

( 2 ) INFORMATION FOR SEQ ID NO:4:

( i ) SEQUENCE CHARACTERISTICS:
        ( A ) LENGTH: 24 bases
        ( B ) TYPE: nucleic acid (C) STRANDEDNESS: single
(D) TOPOLOGY: linear (ii) MOLECULE TYPE: DNA (synthetic)

(xi) SEQUENCE DESCRIPTION: SEQ ID NO:4:

TTTAGATCGT MTTGARTTTR T W CC         24

(2) INFORMATION FOR SEQ ID NO:5:

(i) SEQUENCE CHARACTERISTICS:
    (A) LENGTH: 23 bases
    (B) TYPE: nucleic acid
    (C) STRANDEDNESS: single
    (D) TOPOLOGY: linear (ii) MOLECULE TYPE: DNA (synthetic)

(xi) SEQUENCE DESCRIPTION: SEQ ID NO:5:

AGGAACAAAY TCAAK W CGRT CTA           23

(2) INFORMATION FOR SEQ ID NO:6:

(i) SEQUENCE CHARACTERISTICS:
    (A) LENGTH: 24 bases
    (B) TYPE: nucleic acid
    (C) STRANDEDNESS: single
    (D) TOPOLOGY: linear (ii) MOLECULE TYPE: DNA (synthetic)

(xi) SEQUENCE DESCRIPTION: SEQ ID NO:6:

TATAGATAGA ATCGAATTYV TBCC            24

(2) INFORMATION FOR SEQ ID NO:7:

(i) SEQUENCE CHARACTERISTICS:
    (A) LENGTH: 23 bases
    (B) TYPE: nucleic acid
    (C) STRANDEDNESS: single
    (D) TOPOLOGY: linear (ii) MOLECULE TYPE: DNA (synthetic)

(xi) SEQUENCE DESCRIPTION: SEQ ID NO:7:

TATAGATAAA ATAGAATTKR THC             23

(2) INFORMATION FOR SEQ ID NO:8:

(i) SEQUENCE CHARACTERISTICS:
    (A) LENGTH: 23 bases
    (B) TYPE: nucleic acid
    (C) STRANDEDNESS: single
    (D) TOPOLOGY: linear (ii) MOLECULE TYPE: DNA (synthetic)

(xi) SEQUENCE DESCRIPTION: SEQ ID NO:8:

TATAGATAGA AT W GAATTYR TNC           23

(2) INFORMATION FOR SEQ ID NO:9:

(i) SEQUENCE CHARACTERISTICS:
    (A) LENGTH: 21 bases
    (B) TYPE: nucleic acid
    (C) STRANDEDNESS: single
    (D) TOPOLOGY: linear (ii) MOLECULE TYPE: DNA (synthetic)

(xi) SEQUENCE DESCRIPTION: SEQ ID NO:9:

GAATAAATTC TATTYBVTCT A                                                         21

( 2 ) INFORMATION FOR SEQ ID NO:10:

( i ) SEQUENCE CHARACTERISTICS:
        ( A ) LENGTH: 22 bases
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:10:

GGAACAAAYT CAAKYCGRTC TA                                                        22

( 2 ) INFORMATION FOR SEQ ID NO:11:

( i ) SEQUENCE CHARACTERISTICS:
        ( A ) LENGTH: 22 bases
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:11:

GGAATAAATT CAATTK W RTC  W A                                                    22

( 2 ) INFORMATION FOR SEQ ID NO:12:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:12:

Gly Pro Gly Phe Thr Gly Gly Asp
     1               5

( 2 ) INFORMATION FOR SEQ ID NO:13:

( i ) SEQUENCE CHARACTERISTICS:
        ( A ) LENGTH: 24 bases
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:13:

GGACCAGGAT TTACAGGAGG AGAT                                                      24

( 2 ) INFORMATION FOR SEQ ID NO:14:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:14:

Xaa Xaa Xaa Leu Lys Xaa Xaa Xaa Arg Tyr
     1               5                      10

( 2 ) INFORMATION FOR SEQ ID NO:15:

( i ) SEQUENCE CHARACTERISTICS:
  ( A ) LENGTH: 29 bases
  ( B ) TYPE: nucleic acid
  ( C ) STRANDEDNESS: single
  ( D ) TOPOLOGY: linear ( i i ) MOLECULE TYPE: DNA (synthetic)

( x i ) SEQUENCE DESCRIPTION: SEQ ID NO:15:

TAACGTGTAT W CGSTTTTAA TTT W GAYTC    29

( 2 ) INFORMATION FOR SEQ ID NO:16:

( i ) SEQUENCE CHARACTERISTICS:
  ( A ) LENGTH: 29 bases
  ( B ) TYPE: nucleic acid
  ( C ) STRANDEDNESS: single
  ( D ) TOPOLOGY: linear ( i i ) MOLECULE TYPE: DNA (synthetic)

( x i ) SEQUENCE DESCRIPTION: SEQ ID NO:16:

GAATCAAAAT TAAAAGCM W A TACMMGHTA    29

( 2 ) INFORMATION FOR SEQ ID NO:17:

( i ) SEQUENCE CHARACTERISTICS:
  ( A ) LENGTH: 14 amino acids
  ( B ) TYPE: amino acid
  ( C ) STRANDEDNESS: single
  ( D ) TOPOLOGY: linear ( i i ) MOLECULE TYPE: protein ( x i ) SEQUENCE DESCRIPTION: SEQ ID NO:17:

Ala Lys Arg Leu Ser Xaa Xaa Arg Asn Leu Leu Gln Asp Pro
1     5        10

( 2 ) INFORMATION FOR SEQ ID NO:18:

( i ) SEQUENCE CHARACTERISTICS:
  ( A ) LENGTH: 27 bases
  ( B ) TYPE: nucleic acid
  ( C ) STRANDEDNESS: single
  ( D ) TOPOLOGY: linear ( i i ) MOLECULE TYPE: DNA (synthetic)

( x i ) SEQUENCE DESCRIPTION: SEQ ID NO:18:

ATTTCGCTCT TTACTRAGTY GYTTYGC    27

( 2 ) INFORMATION FOR SEQ ID NO:19:

( i ) SEQUENCE CHARACTERISTICS:
  ( A ) LENGTH: 24 bases
  ( B ) TYPE: nucleic acid
  ( C ) STRANDEDNESS: single
  ( D ) TOPOLOGY: linear ( i i ) MOLECULE TYPE: DNA (synthetic)

( x i ) SEQUENCE DESCRIPTION: SEQ ID NO:19:

TTCGTGCTTT GCTCAAASSK YTTG    24

( 2 ) INFORMATION FOR SEQ ID NO:20:

( i ) SEQUENCE CHARACTERISTICS:
  ( A ) LENGTH: 42 bases
  ( B ) TYPE: nucleic acid
  ( C ) STRANDEDNESS: single
  ( D ) TOPOLOGY: linear ( i i ) MOLECULE TYPE: DNA (synthetic)

( x i ) SEQUENCE DESCRIPTION: SEQ ID NO:20:

TGGATCTTGA AGTAAATTCC GTTCATCACT RAGTCGYTTY GC　　　　　　　　　　　　　42

( 2 ) INFORMATION FOR SEQ ID NO:21:

( i ) SEQUENCE CHARACTERISTICS:
　　　　　　　　( A ) LENGTH: 42 bases
　　　　　　　　( B ) TYPE: nucleic acid
　　　　　　　　( C ) STRANDEDNESS: single
　　　　　　　　( D ) TOPOLOGY: linear ( i i ) MOLECULE TYPE: DNA (synthetic)

( x i ) SEQUENCE DESCRIPTION: SEQ ID NO:21:

GCGAAGCGAC TYAGTGATGA RCGGAATTTA CTTCAAGAYY CA　　　　　　　　　　　　42

( 2 ) INFORMATION FOR SEQ ID NO:22:

( i ) SEQUENCE CHARACTERISTICS:
　　　　　　　　( A ) LENGTH: 8 amino acids
　　　　　　　　( B ) TYPE: amino acid
　　　　　　　　( C ) STRANDEDNESS: single
　　　　　　　　( D ) TOPOLOGY: linear ( i i ) MOLECULE TYPE: protein ( x i ) SEQUENCE DESCRIPTION: SEQ ID NO:22:

Gly  Pro  Xaa  Xaa  Xaa  Gly  Gly  Asx
 1                     5

( 2 ) INFORMATION FOR SEQ ID NO:23:

( i ) SEQUENCE CHARACTERISTICS:
　　　　　　　　( A ) LENGTH: 20 bases
　　　　　　　　( B ) TYPE: nucleic acid
　　　　　　　　( C ) STRANDEDNESS: single
　　　　　　　　( D ) TOPOLOGY: linear ( i i ) MOLECULE TYPE: DNA (synthetic)

( x i ) SEQUENCE DESCRIPTION: SEQ ID NO:23:

CCTCCTGTAA ATCY W GGDCC　　　　　　　　　　　　　　　　　　　　　　　　20

( 2 ) INFORMATION FOR SEQ ID NO:24:

( i ) SEQUENCE CHARACTERISTICS:
　　　　　　　　( A ) LENGTH: 23 bases
　　　　　　　　( B ) TYPE: nucleic acid
　　　　　　　　( C ) STRANDEDNESS: single
　　　　　　　　( D ) TOPOLOGY: linear ( i i ) MOLECULE TYPE: DNA (synthetic)

( x i ) SEQUENCE DESCRIPTION: SEQ ID NO:24:

GGACCAGGAT TTACAGG W GG RRA　　　　　　　　　　　　　　　　　　　　　23

( 2 ) INFORMATION FOR SEQ ID NO:25:

( i ) SEQUENCE CHARACTERISTICS:
　　　　　　　　( A ) LENGTH: 12 amino acids
　　　　　　　　( B ) TYPE: amino acid
　　　　　　　　( C ) STRANDEDNESS: single
　　　　　　　　( D ) TOPOLOGY: linear ( i i ) MOLECULE TYPE: protein ( x i ) SEQUENCE DESCRIPTION: SEQ ID NO:25:

Leu  Gly  Pro  Leu  Leu  Gly  Phe  Val  Val  Tyr  Glu  Ile
 1                     5                        10

( 2 ) INFORMATION FOR SEQ ID NO:26:

( i ) SEQUENCE CHARACTERISTICS:
    ( A ) LENGTH: 35 bases
    ( B ) TYPE: nucleic acid
    ( C ) STRANDEDNESS: single
    ( D ) TOPOLOGY: linear ( i i ) MOLECULE TYPE: DNA (synthetic)

( x i ) SEQUENCE DESCRIPTION: SEQ ID NO:26:

TTAGGACCAT TRYT W GGATT TGTTGT W TAT GAAAT      3 5

( 2 ) INFORMATION FOR SEQ ID NO:27:

( i ) SEQUENCE CHARACTERISTICS:
    ( A ) LENGTH: 18 bases
    ( B ) TYPE: nucleic acid
    ( C ) STRANDEDNESS: single
    ( D ) TOPOLOGY: linear ( i i ) MOLECULE TYPE: DNA (synthetic)

( x i ) SEQUENCE DESCRIPTION: SEQ ID NO:27:

CNCCTGCAAY TCA W YA W A      1 8

( 2 ) INFORMATION FOR SEQ ID NO:28:

( i ) SEQUENCE CHARACTERISTICS:
    ( A ) LENGTH: 9 amino acids
    ( B ) TYPE: amino acid
    ( C ) STRANDEDNESS: single
    ( D ) TOPOLOGY: linear ( i i ) MOLECULE TYPE: protein ( x i ) SEQUENCE DESCRIPTION: SEQ ID NO:28:

Asp Arg Asp Val Lys Ile Leu Gly Met
1      5

( 2 ) INFORMATION FOR SEQ ID NO:29:

( i ) SEQUENCE CHARACTERISTICS:
    ( A ) LENGTH: 9 amino acids
    ( B ) TYPE: amino acid
    ( C ) STRANDEDNESS: single
    ( D ) TOPOLOGY: linear ( i i ) MOLECULE TYPE: protein ( x i ) SEQUENCE DESCRIPTION: SEQ ID NO:29:

Asp Arg Asp Val Lys Ile Ile Gly Met
1      5

( 2 ) INFORMATION FOR SEQ ID NO:30:

( i ) SEQUENCE CHARACTERISTICS:
    ( A ) LENGTH: 27 bases
    ( B ) TYPE: nucleic acid
    ( C ) STRANDEDNESS: single
    ( D ) TOPOLOGY: linear ( i i ) MOLECULE TYPE: DNA (synthetic)

( x i ) SEQUENCE DESCRIPTION: SEQ ID NO:30:

GAYAGAGATG T W AAAATY W T AGGAATG      2 7

( 2 ) INFORMATION FOR SEQ ID NO:31:

( i ) SEQUENCE CHARACTERISTICS:

(A) LENGTH: 10 amino acids
(B) TYPE: amino acid
(C) STRANDEDNESS: single
(D) TOPOLOGY: linear (ii) MOLECULE TYPE: protein (xi) SEQUENCE DESCRIPTION: SEQ ID NO:31:

Asp Asp Phe Asn Gln Leu Tyr Lys Val Tyr
1               5                   10

(2) INFORMATION FOR SEQ ID NO:32:

(i) SEQUENCE CHARACTERISTICS:
   (A) LENGTH: 28 bases
   (B) TYPE: nucleic acid
   (C) STRANDEDNESS: single
   (D) TOPOLOGY: linear (ii) MOLECULE TYPE: DNA (synthetic)

(xi) SEQUENCE DESCRIPTION: SEQ ID NO:32:

TGATTTT W MT CAATTATATR AKGTTTAT                                28

(2) INFORMATION FOR SEQ ID NO:33:

(i) SEQUENCE CHARACTERISTICS:
   (A) LENGTH: 8 amino acids
   (B) TYPE: amino acid
   (C) STRANDEDNESS: single
   (D) TOPOLOGY: linear (ii) MOLECULE TYPE: protein (xi) SEQUENCE DESCRIPTION: SEQ ID NO:33:

Val Leu Lys Thr Ala Asn Asp Ile
1               5

(2) INFORMATION FOR SEQ ID NO:34:

(i) SEQUENCE CHARACTERISTICS:
   (A) LENGTH: 23 bases
   (B) TYPE: nucleic acid
   (C) STRANDEDNESS: single
   (D) TOPOLOGY: linear (ii) MOLECULE TYPE: DNA (synthetic)

(xi) SEQUENCE DESCRIPTION: SEQ ID NO:34:

TTMTTAAA W C W GCTAATGAT ATT                                    23

(2) INFORMATION FOR SEQ ID NO:35:

(i) SEQUENCE CHARACTERISTICS:
   (A) LENGTH: 7 amino acids
   (B) TYPE: amino acid
   (C) STRANDEDNESS: single
   (D) TOPOLOGY: linear (ii) MOLECULE TYPE: protein (xi) SEQUENCE DESCRIPTION: SEQ ID NO:35:

Glu Glu Leu Leu Glu Lys Val
1               5

(2) INFORMATION FOR SEQ ID NO:36:

(i) SEQUENCE CHARACTERISTICS:
   (A) LENGTH: 20 bases
   (B) TYPE: nucleic acid
   (C) STRANDEDNESS: single
   (D) TOPOLOGY: linear ( i i ) MOLECULE TYPE: DNA (synthetic)

( x i ) SEQUENCE DESCRIPTION: SEQ ID NO:36:

AAGAGTTAYT ARARAAAGTA 20

( 2 ) INFORMATION FOR SEQ ID NO:37:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:37:

Met Ile His Ala Ala Asp
1               5

( 2 ) INFORMATION FOR SEQ ID NO:38:

( i ) SEQUENCE CHARACTERISTICS:
        ( A ) LENGTH: 19 bases
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:38:

ATGATTCATG CGGCAGATA 19

( 2 ) INFORMATION FOR SEQ ID NO:39:

( i ) SEQUENCE CHARACTERISTICS:
        ( A ) LENGTH: 19 bases
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:39:

TATCTGCCGC ATGAATCAT 19

( 2 ) INFORMATION FOR SEQ ID NO:40:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:40:

Trp Glu Ala Asp Pro Thr Asn Pro
1               5

( 2 ) INFORMATION FOR SEQ ID NO:41:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:41:

```
Asp Trp Glu Ala Asp Leu Asn Asn Ala Gln Leu Arg
1               5                   10
```

( 2 ) INFORMATION FOR SEQ ID NO:42:

( i ) SEQUENCE CHARACTERISTICS:
        ( A ) LENGTH: 36 bases
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:42:

GAGTGGGAAG CAGATCTTAA TAATGCACAA TTAAGG     36

( 2 ) INFORMATION FOR SEQ ID NO:43:

( i ) SEQUENCE CHARACTERISTICS:
        ( A ) LENGTH: 24 bases
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:43:

TGGGAAGMGG ATCCTAMTAA TCCA     24

( 2 ) INFORMATION FOR SEQ ID NO:44:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:44:

```
Thr Asp Tyr His Ile Asp Gln Val Ser Asn Leu Val
1               5                   10
```

( 2 ) INFORMATION FOR SEQ ID NO:45:

( i ) SEQUENCE CHARACTERISTICS:
        ( A ) LENGTH: 25 bases
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:45:

ATACYCGATC GATATGATAR TCCGT     25

( 2 ) INFORMATION FOR SEQ ID NO:46:

( i ) SEQUENCE CHARACTERISTICS:
        ( A ) LENGTH: 28 bases
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:46:

CTAAATTGGA TACTCGATCG ATATGATA     28

( 2 ) INFORMATION FOR SEQ ID NO:47:

( i ) SEQUENCE CHARACTERISTICS:
    ( A ) LENGTH: 28 bases
    ( B ) TYPE: nucleic acid
    ( C ) STRANDEDNESS: single
    ( D ) TOPOLOGY: linear ( i i ) MOLECULE TYPE: DNA (synthetic)

( x i ) SEQUENCE DESCRIPTION: SEQ ID NO:47:

TATCATATCG ATCGAGTATC CAATTTAG                                   28

( 2 ) INFORMATION FOR SEQ ID NO:48:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:48:

Gly Asp Phe Thr Gln Gly Val Met Gly Trp His
    1               5                   10

( 2 ) INFORMATION FOR SEQ ID NO:49:

( i ) SEQUENCE CHARACTERISTICS:
        ( A ) LENGTH: 34 bases
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:49:

GGTGATTTTA CACAAGGGGT AATGGGGTGG CATG                            34

( 2 ) INFORMATION FOR SEQ ID NO:50:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:50:

Lys Ser Lys Ala Leu Ala Glu Leu Gln Gly
    1               5                   10

( 2 ) INFORMATION FOR SEQ ID NO:51:

( i ) SEQUENCE CHARACTERISTICS:
        ( A ) LENGTH: 23 bases
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:51:

AAAGCTCTTG CAGAGTTACA GGG                                        23

( 2 ) INFORMATION FOR SEQ ID NO:52:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:52:

Arg Asn Leu Leu Gln Asp Pro
1               5

( 2 ) INFORMATION FOR SEQ ID NO:53:

( i ) SEQUENCE CHARACTERISTICS:
        ( A ) LENGTH: 20 bases
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:53:

TGGATCT W GD AGTAARTT W C    20

( 2 ) INFORMATION FOR SEQ ID NO:54:

( i ) SEQUENCE CHARACTERISTICS:
        ( A ) LENGTH: 20 bases
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:54:

G W TTYTTACT HC W AGATCCA    20

( 2 ) INFORMATION FOR SEQ ID NO:55:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:55:

Asp Ser Ile Asp Gln Leu Pro Pro
1               5

( 2 ) INFORMATION FOR SEQ ID NO:56:

( i ) SEQUENCE CHARACTERISTICS:
        ( A ) LENGTH: 23 bases
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:56:

GATTCCATTG AYCAATTRCC HCC    23

( 2 ) INFORMATION FOR SEQ ID NO:57:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:57:

Leu Thr Xaa Xaa Val Leu Asp Ile
1               5

( 2 ) INFORMATION FOR SEQ ID NO:58:

( i ) SEQUENCE CHARACTERISTICS:
        ( A ) LENGTH: 23 bases
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:58:

TTAACAMTK W  C W GTATTAGA TAT                                    2 3

( 2 ) INFORMATION FOR SEQ ID NO:59:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:59:

Arg Glu Trp Ile Asn Gly Ala Asn
1               5

( 2 ) INFORMATION FOR SEQ ID NO:60:

( i ) SEQUENCE CHARACTERISTICS:
        ( A ) LENGTH: 22 bases
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:60:

AGARTRK W T W  AATGG W GCKM A W-                                 2 2

( 2 ) INFORMATION FOR SEQ ID NO:61:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:61:

Pro Thr Phe Asp Pro Asp Leu Tyr
1               5

( 2 ) INFORMATION FOR SEQ ID NO:62:

( i ) SEQUENCE CHARACTERISTICS:
        ( A ) LENGTH: 24 bases
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:62:

CC W ACYTTTK ATCCAGATY W  YTAT                                   2 4

( 2 ) INFORMATION FOR SEQ ID NO:63:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:63:

Arg Ile Ile Leu Gly Ser Gly Pro
1               5

( 2 ) INFORMATION FOR SEQ ID NO:64:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:64:

Ser Pro Ile Gly Lys Cys Ala His
1               5

( 2 ) INFORMATION FOR SEQ ID NO:65:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:65:

Pro Ile His Phe Pro Ser Thr
1               5

( 2 ) INFORMATION FOR SEQ ID NO:66:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:66:

Ala Glu Glu Leu Pro Ile Arg Gly Gly Glu Leu
1               5                   10

( 2 ) INFORMATION FOR SEQ ID NO:67:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:67:

Asn Val Met Glu Ser Ser Ala
1               5

( 2 ) INFORMATION FOR SEQ ID NO:68:

( i ) SEQUENCE CHARACTERISTICS:
  ( A ) LENGTH: 9 amino acids
  ( B ) TYPE: amino acid
  ( C ) STRANDEDNESS: single
  ( D ) TOPOLOGY: linear ( i i ) MOLECULE TYPE: protein ( x i ) SEQUENCE DESCRIPTION: SEQ ID NO:68:

Val Ser Ala Ser Thr Val Gln Thr Gly
1               5

( 2 ) INFORMATION FOR SEQ ID NO:69:

( i ) SEQUENCE CHARACTERISTICS:
    ( A ) LENGTH: 10 amino acids
    ( B ) TYPE: amino acid
    ( C ) STRANDEDNESS: single
    ( D ) TOPOLOGY: linear ( i i ) MOLECULE TYPE: protein ( x i ) SEQUENCE DESCRIPTION: SEQ ID NO:69:

His Val Tyr Thr Asn His Cys Val Asp Thr
1               5                   10

( 2 ) INFORMATION FOR SEQ ID NO:70:

( i ) SEQUENCE CHARACTERISTICS:
    ( A ) LENGTH: 8 amino acids
    ( B ) TYPE: amino acid
    ( C ) STRANDEDNESS: single
    ( D ) TOPOLOGY: linear ( i i ) MOLECULE TYPE: protein ( x i ) SEQUENCE DESCRIPTION: SEQ ID NO:70:

Val Ala Ala Glu Ile Gly Leu Gly
1               5

( 2 ) INFORMATION FOR SEQ ID NO:71:

( i ) SEQUENCE CHARACTERISTICS:
    ( A ) LENGTH: 22 bases
    ( B ) TYPE: nucleic acid
    ( C ) STRANDEDNESS: single
    ( D ) TOPOLOGY: linear ( i i ) MOLECULE TYPE: DNA (synthetic)

( x i ) SEQUENCE DESCRIPTION: SEQ ID NO:71:

GAATTATACT TGGTTCAGGC CC                                      22

( 2 ) INFORMATION FOR SEQ ID NO:72:

( i ) SEQUENCE CHARACTERISTICS:
    ( A ) LENGTH: 21 bases
    ( B ) TYPE: nucleic acid
    ( C ) STRANDEDNESS: single
    ( D ) TOPOLOGY: linear ( i i ) MOLECULE TYPE: DNA (synthetic)

( x i ) SEQUENCE DESCRIPTION: SEQ ID NO:72:

GTCCAATCGG AAAATGTGCC C                                       21

( 2 ) INFORMATION FOR SEQ ID NO:73:

( i ) SEQUENCE CHARACTERISTICS:
    ( A ) LENGTH: 20 bases
    ( B ) TYPE: nucleic acid
    ( C ) STRANDEDNESS: single -continued (D) TOPOLOGY: linear (ii) MOLECULE TYPE: DNA (synthetic)

(xi) SEQUENCE DESCRIPTION: SEQ ID NO:73:

CCAATTCACT TCCCATCGAC                                                         20

(2) INFORMATION FOR SEQ ID NO:74:

(i) SEQUENCE CHARACTERISTICS:
        (A) LENGTH: 31 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:74:

GCTGAAGAAC TTCCTATTCG TGGTGGTGAG C                                            31

(2) INFORMATION FOR SEQ ID NO:75:

(i) SEQUENCE CHARACTERISTICS:
        (A) LENGTH: 19 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:75:

CGTTATGGAG AGCAGCGCA                                                          19

(2) INFORMATION FOR SEQ ID NO:76:

(i) SEQUENCE CHARACTERISTICS:
        (A) LENGTH: 26 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:76:

GTTAGCGCAT CAACAGTCCA AACGGG                                                  26

(2) INFORMATION FOR SEQ ID NO:77:

(i) SEQUENCE CHARACTERISTICS:
        (A) LENGTH: 30 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:77:

CATGTTTATA CTAACCATTG TGTGGATACG                                              30

(2) INFORMATION FOR SEQ ID NO:78:

(i) SEQUENCE CHARACTERISTICS:
        (A) LENGTH: 25 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:78:

CGTAGCAGCA GAAATCGGCT TGGGC                                                   25

( 2 ) INFORMATION FOR SEQ ID NO:79:

( i ) SEQUENCE CHARACTERISTICS:
    ( A ) LENGTH: 8 amino acids
    ( B ) TYPE: amino acid
    ( C ) STRANDEDNESS: single
    ( D ) TOPOLOGY: linear ( i i ) MOLECULE TYPE: protein ( x i ) SEQUENCE DESCRIPTION: SEQ ID NO:79:

Gly Gly Thr Asn Met Asn Pro Ile
1               5

( 2 ) INFORMATION FOR SEQ ID NO:80:

( i ) SEQUENCE CHARACTERISTICS:
    ( A ) LENGTH: 10 amino acids
    ( B ) TYPE: amino acid
    ( C ) STRANDEDNESS: single
    ( D ) TOPOLOGY: linear ( i i ) MOLECULE TYPE: protein ( x i ) SEQUENCE DESCRIPTION: SEQ ID NO:80:

Gly Tyr Pro Leu Ala Asn Asp Leu Gln Gly
1               5                   10

( 2 ) INFORMATION FOR SEQ ID NO:81:

( i ) SEQUENCE CHARACTERISTICS:
    ( A ) LENGTH: 26 bases
    ( B ) TYPE: nucleic acid
    ( C ) STRANDEDNESS: single
    ( D ) TOPOLOGY: linear ( i i ) MOLECULE TYPE: DNA (synthetic)

( x i ) SEQUENCE DESCRIPTION: SEQ ID NO:81:

GGGAGGAACA AATATGAATC CTTATC                                           2 6

( 2 ) INFORMATION FOR SEQ ID NO:82:

( i ) SEQUENCE CHARACTERISTICS:
    ( A ) LENGTH: 32 bases
    ( B ) TYPE: nucleic acid
    ( C ) STRANDEDNESS: single
    ( D ) TOPOLOGY: linear ( i i ) MOLECULE TYPE: DNA (synthetic)

( x i ) SEQUENCE DESCRIPTION: SEQ ID NO:82:

CAGGCTATCC GTTAGCGAAT GACTTACAAG GG                                    3 2

( 2 ) INFORMATION FOR SEQ ID NO:83:

( i ) SEQUENCE CHARACTERISTICS:
    ( A ) LENGTH: 7 amino acids
    ( B ) TYPE: amino acid
    ( C ) STRANDEDNESS: single
    ( D ) TOPOLOGY: linear ( i i ) MOLECULE TYPE: protein ( x i ) SEQUENCE DESCRIPTION: SEQ ID NO:83:

Asn Val Gly Ala Val Ser Trp
1               5

( 2 ) INFORMATION FOR SEQ ID NO:84:

( i ) SEQUENCE CHARACTERISTICS:
   ( A ) LENGTH: 8 amino acids
   ( B ) TYPE: amino acid
   ( C ) STRANDEDNESS: single
   ( D ) TOPOLOGY: linear ( i i ) MOLECULE TYPE: protein ( x i ) SEQUENCE DESCRIPTION: SEQ ID NO:84:

Tyr Asn Gly Tyr Leu Gly Ala Gln
1               5

( 2 ) INFORMATION FOR SEQ ID NO:85:

( i ) SEQUENCE CHARACTERISTICS:
      ( A ) LENGTH: 22 bases
      ( B ) TYPE: nucleic acid
      ( C ) STRANDEDNESS: single
      ( D ) TOPOLOGY: linear ( i i ) MOLECULE TYPE: DNA (synthetic)

( x i ) SEQUENCE DESCRIPTION: SEQ ID NO:85:

AATGTTGGCG CGGTCAGCTG GG                                    22

( 2 ) INFORMATION FOR SEQ ID NO:86:

( i ) SEQUENCE CHARACTERISTICS:
      ( A ) LENGTH: 24 bases
      ( B ) TYPE: nucleic acid
      ( C ) STRANDEDNESS: single
      ( D ) TOPOLOGY: linear ( i i ) MOLECULE TYPE: DNA (synthetic)

( x i ) SEQUENCE DESCRIPTION: SEQ ID NO:86:

TACAATGGCT ATTTAGGTGC ACAG                                  24

( 2 ) INFORMATION FOR SEQ ID NO:87:

( i ) SEQUENCE CHARACTERISTICS:
      ( A ) LENGTH: 7 amino acids
      ( B ) TYPE: amino acid
      ( C ) STRANDEDNESS: single
      ( D ) TOPOLOGY: linear ( i i ) MOLECULE TYPE: protein ( x i ) SEQUENCE DESCRIPTION: SEQ ID NO:87:

Ile Xaa Ser Glu Asp Gly Glu
1               5

( 2 ) INFORMATION FOR SEQ ID NO:88:

( i ) SEQUENCE CHARACTERISTICS:
      ( A ) LENGTH: 20 bases
      ( B ) TYPE: nucleic acid
      ( C ) STRANDEDNESS: single
      ( D ) TOPOLOGY: linear ( i i ) MOLECULE TYPE: DNA (synthetic)

( x i ) SEQUENCE DESCRIPTION: SEQ ID NO:88:

ATT W CYTCAG AAGATGGAGA                                     20

( 2 ) INFORMATION FOR SEQ ID NO:89:

( i ) SEQUENCE CHARACTERISTICS:
      ( A ) LENGTH: 19 bases
      ( B ) TYPE: nucleic acid
      ( C ) STRANDEDNESS: single
      ( D ) TOPOLOGY: linear ( i i ) MOLECULE TYPE: DNA (synthetic)

( x i ) SEQUENCE DESCRIPTION: SEQ ID NO:89:

TCTCCATCTT CTGARG W AA 19

We claim:

1. A nucleotide sequence useful as a probe for identifying a gene coding for a *Bacillus thuringiensis* toxin, wherein said nucleotide sequence encodes a peptide selected from the group consisting of SEQ ID NO. 1, SEQ ID NO. 14, SEQ ID NO. 17, SEQ ID NO. 22, SEQ ID NO. 25, SEQ ID NO. 28, SEQ ID NO. 29, SEQ ID NO. 31, SEQ ID NO. 33, SEQ ID NO. 35, SEQ ID NO. 40, SEQ ID NO. 41, SEQ ID NO. 44, SEQ ID NO. 52, SEQ ID NO. 55, SEQ ID NO. 57, SEQ ID NO. 59, SEQ ID NO. 61, SEQ ID NO. 79, SEQ ID NO. 80, SEQ ID NO. 83, SEQ ID NO. 84, and SEQ ID NO. 87, wherein said nucleotide sequence is not one of the following sequences: SEQ ID NO. 13, SEQ ID NO. 38, SEQ ID NO. 49, SEQ ID NO. 51, SEQ ID NO. 71, SEQ ID NO. 72, SEQ ID NO. 73, SEQ ID NO. 74, SEQ ID NO. 75, SEQ ID NO. 76, SEQ ID NO. 77, SEQ ID NO. 78, SEQ ID NO. 81, SEQ ID NO. 82, SEQ ID NO. 85, and SEQ ID NO. 86.

2. A nucleotide sequence useful as a probe for identifying a gene coding for a *Bacillus thuringiensis* toxin, wherein said nucleotide sequence is selected from the group consisting of SEQ ID NO. 2, SEQ ID NO. 3, SEQ ID NO. 4, SEQ ID NO. 5, SEQ ID NO. 6, SEQ ID NO. 7, SEQ ID NO. 8, SEQ ID NO. 9, SEQ ID NO. 10, SEQ ID NO. 11, SEQ ID NO. 15, SEQ ID NO. 16, SEQ ID NO. 18, SEQ ID NO. 19, SEQ ID NO. 20, SEQ ID NO. 21, SEQ ID NO. 23, SEQ ID NO. 24, SEQ ID NO. 26, SEQ ID NO. 27, SEQ ID NO. 30, SEQ ID NO. 32, SEQ ID NO. 34, SEQ ID NO. 36, SEQ ID NO. 39, SEQ ID NO. 42, SEQ ID NO. 43, SEQ ID NO. 45, SEQ ID NO. 46, SEQ ID NO. 47, SEQ ID NO. 53, SEQ ID NO. 54, SEQ ID NO. 56, SEQ ID NO. 58, SEQ ID NO. 60, SEQ ID NO. 62, SEQ ID NO. 88, and SEQ ID NO. 89.

3. A nucleic acid probe consisting of a labeled DNA wherein said DNA encodes a peptide selected from the group consisting of SEQ ID NO. 1, SEQ ID NO. 14, SEQ ID NO. 17, SEQ ID NO. 22, SEQ ID NO. 25, SEQ ID NO. 28, SEQ ID NO. 29, SEQ ID NO. 31, SEQ ID NO. 33, SEQ ID NO. 35, SEQ ID NO. 40, SEQ ID NO. 41, SEQ ID NO. 44, SEQ ID NO. 52, SEQ ID NO. 55, SEQ ID NO. 57, SEQ ID NO. 59, SEQ ID NO. 61, SEQ ID NO. 79, SEQ ID NO. 80, SEQ ID NO. 83, SEQ ID NO. 84, and SEQ ID NO. 87, wherein said nucleotide sequence is not one of the following sequences: SEQ ID NO. 13, SEQ ID NO. 38, SEQ ID NO. 49, SEQ ID NO. 51, SEQ ID NO. 71, SEQ ID NO. 72, SEQ ID NO. 73, SEQ ID NO. 74, SEQ ID NO. 75, SEQ ID NO. 76, SEQ ID NO. 77, SEQ ID NO. 78, SEQ ID NO. 81, SEQ ID NO. 82, SEQ ID NO. 85, and SEQ ID NO. 86.

4. The nucleic acid probe, according to claim 3, wherein said nucleotide sequence is selected from the group consisting of SEQ ID NO. 2, SEQ ID NO. 3, SEQ ID NO. 4, SEQ ID NO. 5, SEQ ID NO. 6, SEQ ID NO. 7, SEQ ID NO. 8, SEQ ID NO. 9, SEQ ID NO. 10, SEQ ID NO. 11, SEQ ID NO. 15, SEQ ID NO. 16, SEQ ID NO. 18, SEQ ID NO. 19, SEQ ID NO. 20, SEQ ID NO. 21, SEQ ID NO. 23, SEQ ID NO. 24, SEQ ID NO. 26, SEQ ID NO. 27, SEQ ID NO. 30, SEQ ID NO. 32, SEQ ID NO. 34, SEQ ID NO. 36, SEQ ID NO. 39, SEQ ID NO. 42, SEQ ID NO. 43, SEQ ID NO. 45, SEQ ID NO. 46, SEQ ID NO. 47, SEQ ID NO. 53, SEQ ID NO. 54, SEQ ID NO. 56, SEQ ID NO. 58, SEQ ID NO. 60, SEQ ID NO. 62, SEQ ID NO. 88, and SEQ ID NO. 89.

* * * * *

UNITED STATES PATENT AND TRADEMARK OFFICE
CERTIFICATE OF CORRECTION

PATENT NO. : 5,430,137
DATED : July 4, 1995
INVENTOR(S) : Frank H. Gaertner, August J. Sick, Mark Thompson, H. Ernest Schnepf, George E. Schwab, Kenneth E. Narva It is certified that error appears in the above-indentified patent and that said Letters Patent is hereby corrected as shown below:

Column 2: line 57: "5, F or L;" should read --5, I or F or L;--; lines 60-61: "5'-"T" should read --"5'-T--; line 62: "A"3'" should read --A-3'"--; line 63: "C"-3'" should read --C-3'--".

Column 3: line 9: "AAATFCAATT" should read --AAATTCAATT--; line 14: "GPGFFGGD" should read --GPGFTGGD--.

Column 4: line 16: "G""" should read --G-3'"--; line 26: "T-3' + (SEQ" should read --T-3'" (SEQ--; line 63: "CAGATCTTAA" should read --CAGATCTTAA--; line 65: "GGATCCTA" should read --GGATCCTA--.

Column 5: line 6: "CGATCGATA" should read --CGATCGATA--; line 8: "CGATCGATA" should read --CGATCGATA--; line 9: "TATCGATCGAGT" should read --TATCGATCGAGT--; lines 19-20: "G" (SEQ ID NO. 49) 3'" should read --G-3'" (SEQ ID NO. 49)--; lines 25-26: "G" (SEQ ID NO. 51) 3'" should read --G-3'" (SEQ ID NO. 51)--; line 22: "KSKAIAELQG" should read --"KSKALAELQG"--; lines 33-34: "C" (SEQ ID NO. 53) 3'" should read --C-3'" (SEQ ID NO. 53)--;

UNITED STATES PATENT AND TRADEMARK OFFICE
CERTIFICATE OF CORRECTION

PATENT NO. : 5,430,137
DATED : July 4, 1995
INVENTOR(S) : Frank H. Gaertner, August J. Sick, Mark Thompson, H. Ernest Schnepf, George E. Schwab, Kenneth E. Narva It is certified that error appears in the above-indentified patent and that said Letters Patent is hereby corrected as shown below:

Column 5: lines 45-46: "C" (SEQ ID NO. 56) 3'" should read --C-3'" (SEQ ID NO. 56)--.
Column 9: line 29: "a 2peptide" should read --a peptide--.
Column 19: group 14/87, 3rd line: "omitted", should read --995 coleopterans--.

Signed and Sealed this

Twelfth Day of March, 1996

Attest:

BRUCE LEHMAN

Attesting Officer      Commissioner of Patents and Trademarks